(12) United States Patent
Crabtree et al.

(10) Patent No.: US 7,427,684 B2
(45) Date of Patent: Sep. 23, 2008

(54) PROCESS FOR THE PRODUCTION OF LACTAMS

(75) Inventors: Simon Peter Crabtree, Durham City (GB); Derek Vincent Tyers, Thirsk (GB); Mohammed Sharif, Middlesborough (GB)

(73) Assignee: Davy Process Technology Limited, London (GB)

( * ) Notice: Subject to any disclaimer, the term of this patent is extended or adjusted under 35 U.S.C. 154(b) by 0 days.

(21) Appl. No.: 10/577,629

(22) PCT Filed: Oct. 15, 2004

(86) PCT No.: PCT/GB2004/004388

§ 371 (c)(1),
(2), (4) Date: Feb. 7, 2007

(87) PCT Pub. No.: WO2005/051907

PCT Pub. Date: Jun. 9, 2005

(65) Prior Publication Data

US 2007/0244317 A1 Oct. 18, 2007

(30) Foreign Application Priority Data

Oct. 30, 2003 (GB) .................................. 0325384.6

(51) Int. Cl.
*C07D 207/00* (2006.01)
*C07D 307/20* (2006.01)
*C07C 31/18* (2006.01)

(52) U.S. Cl. ....................... 548/400; 549/295; 549/302; 568/852

(58) Field of Classification Search .................. None
See application file for complete search history.

(56) References Cited

U.S. PATENT DOCUMENTS

| | | | |
|---|---|---|---|
| 2,351,939 A | 6/1944 | Drossbach et al. |
| 2,843,600 A | 7/1958 | McKeever |
| 3,080,377 A | 3/1963 | Liao |
| 3,109,005 A | 10/1963 | Lidov |
| 3,637,743 A | 1/1972 | Prince |
| 3,957,827 A | 5/1976 | Lyons |
| 4,263,175 A | 4/1981 | Pesa et al. |
| 4,356,124 A | 10/1982 | Pesa et al. |
| 4,485,245 A | 11/1984 | Hsu et al. |
| 4,485,246 A | 11/1984 | Lyons |
| 4,892,955 A | 1/1990 | Wada et al. |
| 4,931,573 A | 6/1990 | Wada et al. |
| 5,021,589 A | 6/1991 | Wada et al. |
| 5,047,561 A | 9/1991 | Miyazawa et al. |
| 5,077,442 A | 12/1991 | Hara et al. |
| 5,079,372 A | 1/1992 | Wada et al. |
| 5,434,273 A | 7/1995 | Weyer et al. |
| 5,580,991 A | 12/1996 | Sugiyama et al. |
| 5,912,358 A | 6/1999 | Frohn et al. |
| 6,008,375 A | 12/1999 | Bergfeld et al. |

FOREIGN PATENT DOCUMENTS

| | | |
|---|---|---|
| GB | 976939 | 12/1964 |
| GB | 2 055 798 A | 3/1981 |
| JP | 02-075716 | 3/1990 |
| JP | 02121976 A | 5/1990 |
| JP | 02200680 A | 8/1990 |
| JP | 02207081 A | 8/1990 |
| JP | 02233674 A | 9/1990 |
| JP | 02235880 A | 9/1990 |
| JP | 03074377 A | 3/1991 |
| JP | 03083974 A | 4/1991 |
| JP | 03112973 A | 5/1991 |
| JP | 03141273 A | 6/1991 |
| JP | 03204870 A | 9/1991 |
| JP | 04091085 A | 3/1992 |
| JP | 04217636 A | 8/1992 |
| JP | 06107654 A | 4/1994 |
| JP | 06172338 A | 6/1994 |
| JP | 07033756 A | 2/1995 |
| JP | 07082260 A | 3/1995 |
| WO | WO 96/23803 A1 | 8/1996 |
| WO | WO 02/102772 A1 | 12/2002 |
| WO | WO 03/093208 A1 | 11/2003 |

OTHER PUBLICATIONS

H. Inagaki, S. Nishimura, Y. Hara, K. Wada, "Hydrogenation Reaction of Carbonyl Compounds Catalyzed by Cationic Ruthenium Complexes," Science and Technology in Catalysis 1994, pp. 327-330.

Y. Hara, K. Wada, "Hydrogenation Reaction of Carboxylic Anhydrides Catalyzed by a New and Highly Active Cationic Ruthenium Complex," Chemistry Letters 1991, pp. 553-554.

(Continued)

*Primary Examiner*—Sikarl A Witherspoon
(74) *Attorney, Agent, or Firm*—McDonnell Boehnen Hulbert & Berghoff LLP

(57) ABSTRACT

A homogeneous process for the hydrogenation of dicarboxylic acid and/or derivative thereof with an amine in the presence of a catalyst comprising: (a) ruthenium or osmium; and (b) an organic phosphine; and wherein the hydrogenation is carried out in the presence of water.

32 Claims, No Drawings

OTHER PUBLICATIONS

R.A. Grey, G.P. Pez, A. Wallo, "Anionic Metal Hydride Catalysts. 2. Application to the Hydrogenation of Ketones, Aldehydes, Carboxylic Acid Esters, and Nitriles," Journal of the American Chemical Society 1981, No. 103, pp. 7536-7542.

U. Matteoli, G. Menchi, M. Bianchi, F. Piacenti, "Homogeneous Catalytic Hydrogenation of the Esters of Bicarboxylic Acids -Part III. EthyleneGlycol from Dimethyl Oxalate," Journal of Molecular Catalysis, No. 44, 1988, pp. 347-355.

U. Matteoli, G. Menchi, M. Bianchi, F. Piacenti, S, Ianelli, M. Nardelli, "Structure and Catalytic Activity of Phosphine-substituted Ruthenium Carbonyl Carboxylates," Journal of Organometallic Chemistry, vol. 498, 1995, pp. 177-186.

H. Teunissen, C.J. Elsevier, "Ruthenium Catalysed Hydrogenation of Dimethyl Oxalate to Ethylene Glycol," Chemical Communications, 1997, pp. 667-668.

H.T. Teunissen, C.J. Elsevier, Homogeneous Ruthenium Catalyzed Hydrogenation of Esters to Alcohols, Chemical Communications, 1998, pp. 1367-1368.

PROCESS FOR THE PRODUCTION OF LACTAMS

This application claims priority under 35 U.S.C. § 119, via the Paris Convention for the Protection of Industrial Property, to International Application No. PCT/GB2004/004388, filed Oct. 15, 2004, and to GB 0325384.6, filed Oct. 30, 2003, which are hereby incorporated by reference.

TECHNICAL FIELD

The present invention relates to a homogeneous process for the hydrogenation of dicarboxylic acids and/or derivatives thereof. More particularly, it relates to a homogeneous hydrogenation process for the production of lactams from dicarboxylic acids and/or derivatives thereof and an amine. Most particularly it relates to a homogeneous hydrogenation process for the production of lactams from dicarboxylic acids and/or derivatives thereof and an amine which can be carried out in the presence of water.

BACKGROUND

Lactams such as N-methyl pyrrolidone and other pyrrolidones are conventionally produced from γ-butyrolactone and the appropriate amine. The γ-butyrolactone itself is generally produced from the hydrogenation of maleic esters in the vapour phase. The maleic esters are produced from maleic anhydride which in turn is produced from the oxidation of butane. In view of the large number of steps present, the cost of the process is high and since N-methyl pyrrolidone and other pyrrolidones are commercially important commodity chemicals it is desirable to provide a process which gives a cost-effective route to the lactam.

SUMMARY OF THE PRESENT INVENTION

Many suggestions have been made in an attempt to overcome this problem and various processes have been suggested in which the lactam is produced in one step from the dicarboxylic acid or anhydride and the appropriate amine in the presence of a heterogeneous catalyst. However, these processes often require exotic catalysts which are expensive. Alternatively, the processes require mixtures of metal catalysts. Unfortunately, such processes suffer from difficulties in recycling the catalyst which adds to the cost of the process. For example, U.S. Pat. No. 5,912,358 suggests the use of a mixed metal catalyst of palladium and rhenium on a support such as alumina and U.S. Pat. No. 4,356,124 and U.S. Pat. No. 4,263,175 which use a heterogeneous ruthenium oxide based catalyst mixed with other transition metals such as iron and nickel.

DETAILED DESCRIPTION OF THE PRESENT INVENTION

Other heterogeneous processes have been suggested. For example in GB 976939 a cobalt, copper, nickel and/or iron catalyst is used and excess ammonia and a high pressure is required. U.S. Pat. No. 3,109,005 requires the absence of water and also requires a high pressure.

Many catalyst systems are known which are suitable for the hydrogenation of carboxylic acids, and/or derivatives thereof. Traditionally, such reactions are carried out using heterogeneous catalysts and often require high temperatures and pressures. A disadvantage of these heterogeneous catalyst systems is that many are intolerant of acid feedstocks and therefore have limited use.

Catalysts have been suggested for the hydrogenation of carboxylic acids and their derivatives based on ruthenium/phosphine systems. Examples of these catalyst systems includes those described in U.S. Pat. No. 5,047,561, U.S. Pat. No. 5,079,372, U.S. Pat. No. 5,580,991, U.S. Pat. No. 5,077,442, U.S. Pat. No. 5,021,589, U.S. Pat. No. 4,931,573, U.S. Pat. No. 4,892,955, "Hydrogenation reaction of carboxylic anhydrides catalysed by a new and highly active cationic ruthenium complex", "Y-Hara et al Chem Lett (1991) 553, U.S. Pat. No. 3,957,827, U.S. Pat. No. 4,485,245 and U.S. Pat. No. 4,480,115 which are incorporated herein by reference.

However, whilst the systems described in these documents provide processes which in general adequately enable hydrogenation reactions to be carried out, they do suffer from certain disadvantages and drawbacks. In particular, they require that the hydrogenation is carried out in the absence of water since it is believed that any water present inhibits the catalyst or significantly reduces the rate of reaction. For example, in U.S. Pat. No. 5,047,561 an organic solvent is used and it is stated that the amount of water present should be controlled and should be no higher than 1% by weight. In "Hydrogenation reaction of carbonyl compounds catalysed by cationic ruthenium complexes", H-Inagaki et al, Science and Technology of Catalysis (1994) 327 it is explained that the presence of water retards the hydrogenation reaction of succinic anhydride in the presence of a ruthenium trialkyl phosphine complex in the presence of a promotor and that it is necessary to remove the water produced by hydrogenation in the gas stream and in U.S. Pat. No. 3,957,827 and U.S. Pat. No. 4,485,245 scavengers are used to remove any water produced in the reaction with the aim of improving yield and productivity.

Many of these known catalyst systems also require the presence of a promotor to increase the selectivity and activity of the ruthenium catalyst. Examples of this include U.S. Pat. No. 5,079,372 and U.S. Pat. No. 4,931,573 where reactions are carried out in the presence of an organic solvent and a metal selected from Group IVA, VA and III is required as a promotor.

Another example of the use of a promotor may be found in U.S. Pat. No. 5,077,442. In this case a phosphorous compound is used to promote selectivity and conversion. This document teaches that any water produced in the reaction is removed from the reaction zone as the presence of water is said to decrease selectivity and conversion.

Another suitable promotor described is a conjugate base of an acid and in this connection reference may be made back to U.S. Pat. No. 5,021,589 and U.S. Pat. No. 4,892,955. In this latter case, it is noted that components of the catalyst system are susceptible to hydrolysis under the reaction conditions and that a hydrogen purge was required to remove water produced during the reaction.

In view of the foregoing it will be understood that there is still a need for a process for the production of lactams in a cost-effective manner from readily available starting materials. This can be achieved by the homogeneous hydrogenation of dicarboxylic acids and derivatives thereof with the appropriate amine using a ruthenium/phosphine catalyst system in the presence of water. Surprisingly, despite the teachings of the prior art, it has been established that the presence of water is not only not disadvantageous but indeed offers positive advantages.

Thus according to the present invention there is provided a homogeneous process for the hydrogenation of dicarboxylic acid and/or derivative thereof with amine in the presence of a catalyst comprising:

(a) ruthenium or osmium; and (b) an organic phosphine;

and wherein the hydrogenation is carried out in the presence of water.

By "homogeneous process" we mean that the catalyst is dissolved in the solvent for the reaction and that at least some of the water present and at least some of the reactants must be in phase with the catalyst. Where excess water and/or excess feedstock is present, the excess may form a separate phase to that comprising the catalyst. Additionally, or alternatively, the product may form a separate phase.

By dicarboxylic acid and/or derivative thereof, we mean one or more compounds comprising any molecule containing at least two carboxylic acid functional groups, for example dicarboxylic acids, polycarboxylic acids, anhydrides, monoesters or diesters of dicarboxylic acids, monoamides or diamides of dicarboxylic acids, salts, such as amine salts, of dicarboxylic acids or mixtures thereof. Preferably the dicarboxylic acid and/or derivative thereof is a $C_4$ to $C_{12}$ dicarboxylic acid. The dicarboxylic acid and/or derivative thereof may be saturated or unsaturated. Particular examples of suitable dicarboxylic acids and/or derivatives thereof include maleic acid, fumaric acid, succinic acid, maleic anhydride, adipic acid, and succinic anhydride. Where more than one dicarboxylic acid and/or derivative thereof is used, they may be of the same functionality, for example both dicarboxylic acids, or may be different, for example a mixture of a dicarboxylic acid and a diester of a dicarboxylic acid.

The amine may be a primary, secondary or tertiary amine. The amine will generally be $NR^1R^2R^3$ where $R^1$, $R^2$ and $R^3$ are each selected from hydrogen or alkyl. Any suitable alkyl group may be used with $C_1$ to $C_6$ being preferred. Most preferably, the alkyl group will be methyl, ethyl or propyl. The selection of the particular amine will depend on the desired product of the reaction. Thus, for example, where N-methyl pyrrolidone is to be prepared, methylamine will be used. A mixture of amines may be used. Without wishing to be bound by any theory, the di- and tri-alkyl amines may be partially hydrolysed under the reaction conditions to produce the mono-alkyl amine and an alcohol. It will be understood that the term amine refers to an amine as defined above or the use of one or more amines which may be of the same or different type. This may be particularly advantageous where a process for producing the desired amine produces a mixture of products. The ability to operate the present process using a mixture of amines enables the step in which the amines must be separated to be avoided. This is particularly advantageous since the separation of amines can be a costly process.

The amine may be mixed with the dicarboxylic acid and/or derivative thereof prior to undergoing the process of the present invention where the amine is mixed with a dicarboxylic acid a salt will generally be formed. In one arrangement the dicarboxylic acid may be converted to the amide or imide by reaction with the amine prior to commencement of the hydrogenation.

Where the reactants are water soluble, the water may be present as the solvent for the reaction. Alternatively, a solvent may be used. Where a solvent is used, the water will be present as an additive in the solvent. In another alternative arrangement, one or both of the reactants or the product of the reaction may be the solvent. In one arrangement at least 1% by weight of water is present.

Where the dicarboxylic acid and/or derivative thereof or the amine is non-water soluble or has low water-solubility, such as for example for where the dicarboxylic acid and/or derivative thereof has a higher carbon content, the reactants or product may be the solvent for the reaction or an organic solvent may be used and the water may be present as an additive. In this case, it may be present in the solvent in any suitable amount and preferably in an amount of up to the solubility limit of the water in the solvent. There may be at least 1% of water present. Additional water may be present in a separate aqueous phase.

In one alternative arrangement, the water may be produced in situ as a by-product of the hydrogenation reaction. Where the water is generated in situ, if maximum benefits are to be achieved, the water should be generated within the first few cycles of the reaction. Where the water is to be generated in situ, an amount of water may be added initially to cover the system's requirements until sufficient water has been generated.

The hydrogen used for the hydrogenation may be impure hydrogen.

It will therefore be understood that the process of the present invention offers substantial advantages over the prior art arrangements in that low cost feedstocks can be used, a homogeneous system may be used and the water need not be removed from any reactants prior to the start of the reaction and may even be present as the solvent. By this means, a cost-effective process is achieved it will also be understood that the production time is reduced.

Further, it has been found that the presence of water is beneficial in terms of catalyst stability. It is noted that in prior art systems, decarbonylation may occur and the carbon monoxide formed is said to strongly inhibit the catalyst. To overcome this it is usual, in prior art arrangements, for the carbon monoxide to be removed and a methanation unit to be included in the plant to deal with the recycling of vent gas to the reactor. However, this is unnecessary in the process of the present invention.

Without wishing to be bound by any theory, it is believed that the presence of water allows a side reaction to occur in the hydrogenation reactor in which any carbon monoxide produced reacts with the water to form carbon dioxide and hydrogen via the water gas shift reaction. This carbon dioxide and hydrogen may be further reacted to form methane. These gases can be readily removed from the reaction system. Thus, this system not only provides a cost-effective hydrogenation process but also reduces the need to have a separate methanation unit in the recycling system for vent gases.

A further advantage of the present invention is that the removal of the carbon monoxide as detailed above allows for effective regeneration of the catalyst. Thus the process offers extended catalyst life which in turn improves the economics of the reaction.

The water gas shift reaction does require heat for its initiation. Where the dicarboxylic acid and/or derivatives thereof or the product of the hydrogenation is not thermally stable at the initial temperature, the process of the present invention can be operated whereby the catalyst is allowed to be inhibited by the presence of generated carbon monoxide, the thermally unstable moiety is removed and the heat is then increased in the presence of the hydrogen such that the water gas shift reaction can operate to reactivate the catalyst for further reaction. By this means the process can be applied to a broad range of dicarboxylic acids or derivatives thereof with prolonged catalyst life.

A still further advantage of the present invention is that there is no requirement to add buffer salts of the kind used in the prior art to stabilise the catalyst and further, promoters are not generally required and, in some circumstances, may even be deleterious.

As detailed above, where the reactants are soluble in water, the water may act as the solvent. However, the method of the present invention may be conducted in the absence of a solvent, i.e. the staring material or reaction product may be a solvent for the reaction. However, if a solvent is used, any suitable solvent may be selected and examples of suitable solvents include, but are not limited to tetraethyleneglycol dimethyl ether, N-methyl pyrrolidone, diethyl ether, ethyleneglycol dimethylether, dioxane, 2-propanol, 2-butanol, secondary alcohols, tertiary alcohols, lactams and N-methyl caprolactam.

The catalyst of the present invention may be a ruthenium/phosphine or an osmium/phosphine catalyst. The ruthenium or osmium is generally provided as a ruthenium or osmium compound although halides are not preferred. Suitable compounds are those which can be converted to active species under the reaction conditions and include nitrates, sulphates, carboxylates, beta diketones, and carbonyls. Ruthenium oxide, carbonyl ruthenates and complex compounds of ruthenium, including hydridophosphineruthenium complexes, may also be used. Specific examples include, but are not limited to, ruthenium nitrate, ruthenium dioxide, ruthenium tetraoxide, ruthenium dihydroxide, ruthenium acetylacetonate, ruthenium acetate, ruthenium maleate, ruthenium succinate, tris-(acetylacetone)ruthenium, pentacarbonylruthenium, dipotassium tetracarbonyl-ruthenium, cyclopentadienyldicarbonyltriruthenium, tetrahydridedecacarbonyltetraruthenium, tetraphenylphosphonium, ruthenium dioxide, ruthenium tetraoxide, ruthenium dihydroxide, bis(tri-n-butylphosphine)tricarbonylruthenium, dodecacarbonyl-triruthenium, and undecacarbonyl-hydride-triruthenate. Corresponding compounds may be used where the catalyst is an osmium/phosphine catalyst.

The ruthenium or osmium compound may be present in any suitable amount. However, it is preferably present in an amount of from 0.0001 to 5 mol, preferably 0.005 to 1 mol, as ruthenium or osmium per liter of reaction solution.

Any suitable phosphine may be used. Compounds which provide tridentate, bidentate and monodentate ligands may be used. Where the metal is ruthenium, tridentate phosphines are particularly preferred. Examples of suitable phosphine compounds include trialkylphosphines, dialkylphosphines, monoalkylphosphines, triarylphosphines, diarylphosphine, monoarylphosphines, diarylmonoalkyl phosphines and dialkylmonoaryl phosphines. Specific examples include but are not limited to tris-1,1,1-(diphenylphosphinomethyl)methane, tris-1,1,1-(diphenylphosphinomethyl)-ethane, tris-1,1,1-(diphenylphosphinomethyl)propane, tris-1,1,1-(diphenylphosphino-methyl)butane, tris-1,1,1-(diphenylphosphinomethyl)-2,2dimethylpropane, tris-1,3,5-(diphenylphosphino-methyl)cyclohexane, tris-1,1,1-(dicyclohexylphosphinomethyl)ethane, tris-1,1,1-(dimethylphosphinomethyl)ethane, tris-1,1,1-(diethylphosphinomethyl)ethane, 1,5,9-triethyl-1,5-9-triphosphacyclododecane, 1,5,9-triphenyl-1,5-9-triphosphacyclododecane, bis(2-diphylephosphinoethyl)phenylphosphine, bis-1,2-(diphenyl phosphino)ethane, bis-1,3-(diphenyl phosphino)propane, bis-1,4-(diphenyl phosphino)butane, bis-1,2-(dimethyl phosphino)ethane, bis-1,3-(diethyl phosphino)propane, bis-1,4-(dicyclohexyl phosphino)butane, tricyclohexylphosphine, trioctyl phosphine, trimethyl phosphine, tripyridyl phosphine, triphenylphosphine with tris-1,1,1-(diphenylphosphinomethyl)-ethane being particularly preferred. Particularly advantageous results are achieved with tridentate facially capped phosphines with tris-1,1,1-(diarylphosphinomethyl)alkane and tris-1,1,1-(dialkylphosphinomethyl)alkane being particularly preferred.

The catalyst may be preformed or generated in-situ. Where an electron rich phosphine such as tris-1,1,1-(diethylphosphinomethyl)ethane, is to be used it may be preferable to preform the complex in the absence of water prior to commencing the process of the present invention.

The phosphine compound may be present in any suitable amount. However, it is preferably present in an amount of from 0.0001 to 5 mol, preferably 0.005 to 1 mol, as phosphine per liter of reaction solution.

Any suitable reaction temperature may be used. However, in the process of the present invention, particular advantages may be noted if the hydrogenation is carried out at temperatures in the region of from about 190° C. to about 300° C., more preferably 230° C. to about 250° C.

Any suitable pressure may be used with a reaction pressure of from about 500 psig to about 2000 psig, being preferred. More preferably a pressure of from 800 psig to 1400 psig may be used and most preferably a pressure of about 1000 psig may be used. However, it will be understood that if a volatile solvent is used a higher reactor pressure may be desirable due to the high partial pressure of the solvent in the reactor.

The reactants may be present in any suitable ratio. Particularly suitable ratios are those from about 0.5:1 to about 100:1 amine to acid or derivative thereof. Preferred ratios include those of from about 0.9:1 to about 2.0:1.

The process may be carried out either in a batch system or in a continuous system. High intensity reactors such as intensive gas/liquid mixing reactors may be used. However, it will be understood that the process of the present invention is particularly suitable for use in a continuous system since the catalyst is not poisoned by carbon monoxide or if poisoning in this way occurs, the catalyst can be regenerated by reaction with the water.

Where the catalyst is removed from the reactor, for example, with a product removal stream, it may be recycled by any suitable means to the reactor. The catalyst may be separated from the product stream by any suitable means. Suitable means include extraction, distillation, gas stripping and membrane separation. In some circumstances, the catalyst may be immobilised on a support to assist recovery. In this arrangement, the immobilised catalyst may be recovered by filtration.

The process of the present invention is particularly suitable for the production of 2-pyrrolidones and the N-alkylated versions thereof. It is also suitable for the production of caprolactam from adipic acid and ammonia and the production of pyrrolidone from maleic acid or anhydride.

The present invention will now be described with reference to the following example which is not intended to be limiting on the scope of the invention.

EXAMPLE 1

This example demonstrates that maleic acid may be successfully hydrogenated in the presence of water and methyl amine to produce N-methyl pyrrolidone.

Ruthenium (III) acetylacetonate (from Johnson Matthey 46 mmols, 0.183 g) and 1,1,1tris(diphenyl-phosphinomethyl) ethane (from Aldrich 6.1 mmols, 0.38 g), water (52.05 g), maleic acid (from Aldrich 173.9 mmols, 20.2 g) 40 wt % methyl amine solution (from Aldrich 30.52 g), 394 mmols methylamine were transferred into a 300 ml Hastelloy Parr autoclave. This was sealed and purged with hydrogen before being pressurised to 600 psig with hydrogen and heated to 250° C. Once 250° C. was achieved the reactor was topped up with hydrogen to 1000 psig and this pressure was maintained throughout the reactor via a regulator. At the end of the reaction the hydrogen supply was isolated and the reaction cooled. At room temperature, the headspace gas was vented. The product was removed from the reactor and weighed (94.2 g, 91.2% mass balance). The water and organic analysis was determined using a Hewlett-Packard gas chromatograph equipped with a micro TCD (wt %): ammonia (1.748) water (80.329), methyl amine (0.662) N-methyl pyrrolidone (15.269) others (0.632); giving a yield of N-methyl pyrrolidone of 83.5 mol % (moles N-methyl pyrrolidone recovered/moles feed).

EXAMPLE 2

This example illustrates that N-methyl succinimide may be successfully hydrogenated in the presence of water to produce N-methyl-pyrrolidone.

Ruthenium (III) acetylacetonate (0.46 mmols, 0.182 g) and 1,1,1tris(diphenyl-phosphino-methyl)ethane (6.1 mmols, 0.38 g), water (69.7 g) N-methyl succinimide (ex Aldrich, 154 mmols, 17.45 g) were transferred into a 300 ml Hastelloy Part autoclave. This was sealed and purged with hydrogen before being pressurised to 600 psig with hydrogen and heated to 250° C. Once 250° C. had been achieved, the reactor was topped up with hydrogen to 1000 psig and this pressure was maintained throughout the reaction via a regulator. At the end of the reaction, after 4 hrs, the hydrogen supply was isolated and the reactor cooled. At room temperature the headspace gas was vented. The product was removed from the reactor and analysed. The water and organic analysis was determined using an HP gas chromatograph equipped with a micro TCD (wt %): ammonia (0.15) water (86.93), NMP (12.52) others (0.392).

EXAMPLE 3

This example illustrates that adipic acid may be successfully hydrogenated in the presence of water and methyl amine to produce N-methyl-caprolactam.

Ruthenium (III) acetylacetonate (0.46 mmols, 0.18 g) and 1,1,1tris(diphenyl-phosphinomethyl)ethane (6.1 mmols, 0.38 g), water (40.14 g) adipic acid (ex Aldrich, 137 mmols, 20.06 g) and 40 wt % methylamine solution (260 mmols, 20.15 g) were transferred into a 300 ml Hastelloy Parr autoclave. This was sealed and purged with hydrogen before being pressurised to 600 psig with hydrogen and heated to 250° C. Once 250° C. had been achieved, the reactor was topped up with hydrogen to 1000 psig and this pressure was maintained throughout the reaction via a regulator. At the end of the reaction, after 4 hrs, the hydrogen supply was isolated and the reactor cooled. At room temperature the headspace gas was vented. The product was removed from the reactor and analysed. The water and organic analysis was determined using an HP gas chromatograph equipped with a micro TCD (area %): ammonia (1.110) water (65.107), methyl amine (0.903) hexahydroazepine (1.191) N-methylhexahydroazepine (1.701) N-methyl caprolactam (16.045) caprolactam (2.706) N,N' dimethyladipamide (1.794) others (9.443).

What is claimed is:

1. A homogenous process for the hydrogenation of dicarboxylic acids and/or derivatives thereof with an amine in the presence of a catalyst comprising:
    (a) ruthenium or osmium; and
    (b) an organic phosphine;

and wherein the hydrogenation is carried out in the presence of water.

2. A homogenous process according to claim 1 wherein the water is present in at least 1% by weight.

3. A homogenous process according to claim 1 wherein the dicarboxylic acid and/or derivative thereof is selected from one or more of dicarboxylic acids, polycarboxylic acids, anhydrides, monoesters or diester of dicarboxylic acids, monoamides or diamides of dicarboxylic acids, salts, such as amine salts, of dicarboxylic acids or mixtures.

4. A homogenous process according to claim 1 wherein the dicarboxylic acid and/or derivative thereof is a $C_4$ to $C_{12}$ dicarboxylic acid.

5. A homogenous process according to claim 1 wherein the dicarboxylic acid and/or derivative thereof is saturated or unsaturated.

6. A homogenous process according to claim 1 wherein the dicarboxylic acid and/or derivative thereof is selected from maleic acid, fumaric acid, succinic acid, maleic anhydride, adipic acid, and succinic anhydride.

7. A homogenous process according to claim 1 wherein the amine is $NR^1R^2R^3$ where $R^1$, $R^2$ and $R^3$ are each hydrogen or alkyl and at least one of $R^1$, $R^2$ and $R^3$ is alkyl.

8. A homogenous process according to claim 7 wherein the alkyl group is a $C_1$ to $C_6$ alkyl group.

9. A homogenous process according to claim 8 wherein the alkyl group is methyl, ethyl or propyl.

10. A homogenous process according to claim 1 wherein the amine is mixed with the dicarboxylic acid and/or derivatives thereof prior to undergoing the process.

11. A homogenous process according to claim 1 wherein the dicarboxylic acid and/or derivative thereof is converted to a corresponding amide by reaction with the amine prior to commencement of the hydrogenation.

12. A homogenous process according to claim 1 wherein the water is present as the solvent for the reaction.

13. A homogenous process according to claim 1 wherein one or both of the reactants or the product of the reaction are the solvent.

14. A homogenous process according to claim 1 wherein a solvent is used and water is present as an additive in the solvent.

15. A homogenous process according to claim 14 wherein the solvent is selected from tetraethyleneglycol dimethyl ether, N-methyl pyrrolidone, diethyl ether, ethyleneglycol dimethylether, dioxane, 2-propanol, 2-butanol, secondary alcohols, tertiary alcohols, lactams and N-methyl caprolactam.

16. A homogenous process according to claim 1 wherein the water is produced in situ as a by-product of the hydrogenation reaction.

17. A homogenous process according to claim 1 wherein the catalyst comprises ruthenium and the ruthenium is provided as a ruthenium compound.

18. A homogenous process according to claim 17 wherein the ruthenium compound is a compound selected from nitrates, sulphates, carboxylates, beta diketones, or carbonyls.

19. A homogenous process according to claim 1 wherein the ruthenium is present in an amount of from 0.005 to 1 mol, as ruthenium per liter of reaction solution.

20. A homogenous process according to claim 1 wherein the phosphine is a tridentate phosphine.

21. A homogenous process according to claim 1 wherein the phosphine is selected from trialkylphosphines, dialkylphosphines, monoalkylphosphines, triarylphosphines, diarylphosphines, monoarylphosphines, diarylmonoalkyl phosphines and dialkylmonoaryl phosphines.

22. A homogenous process according to claim 21 wherein the phosphine is selected from tris-1,1,1-(diphenylphosphinomethyl) methane,
tris-1,1,1-(diphenylphosphinomethyl)ethane,
tris-1,1,1-(diphenylphosphinomethyl)propane,
tris-1,1,1-(diphenylphosphinomethyl)butane,
tris-1,1,1-(diphenylphosphinomethyl)2, 2-dimethylpropane,
tris-1,3,5-(diphenylphosphinomethyl)cyclohexane,
tris-1,1,1-(dicyclohexylphosphinomethyl)ethane,
tris-1,1,1-(dimethylphosphinomethyl)ethane,
tris-1,1,1-(diethylphosphinomethyl)ethane,
1,5,9-triethyl-1,5,9-triphosphacyclododecane,
1,5,9-triphenyl-1,5,9-triphosphacyclododecane,
bis(2-diphenylphosphinoethyl)phenylphosphine,
bis-1,2-(diphenyl phosphino)ethane,
bis-1,3-(diphenyl phosphino)propane,
bis-1,4-(diphenyl phosphino)butane,
bis-1,2-(dimethyl phosphino)ethane,
bis-1,3-(diethyl phosphino)propane,
bis-1,4-(dicyclohexyl phosphino)butane,
tricyclohexylphosphine, trioctylphosphine,
trimethyl phosphine, tripyridyl phosphine and
triphenylphosphine.

23. A homogenous process according to claim 21 wherein the phosphine is selected from
tris-1,1,1-(diarylphosphinomethyl)alkane and
tris-1,1,1-(dialkylphosphinomethyl)alkane.

24. A homogenous process according to claim 1 wherein the catalyst is preformed.

25. A homogenous process according to claim 1 wherein the phosphine compound is present in an amount of from 0.0001 to 5 mol per liter of reaction solution.

26. A homogenous process according to claim 1 wherein the hydrogenation is carried out at temperatures from about 190° C. to about 300° C.

27. A homogenous process according to claim 1 wherein the reaction pressure is from about 500 psig to about 2000 psig.

28. A homogenous process according to claim 1 wherein the ratio of the amine to the dicarboxylic acid or derivative thereof is from about 0.5:1 to about 100:1.

29. A hornogenous process according to claim 1 wherein the ratio of the amine to the dicarboxylic acid or derivative thereof is from about 0.9:1 to about 2.0:1.

30. A homogenous process according to claim 1 wherein the product is a 2-pyrrolidone or an N-alkylated version thereof and the dicarboxylic acid or derivative thereof is maleic acid, maleic anhydride, succinic acid or succinic anhydride.

31. A homogenous process according to claim 1 wherein the product is caprolactam and the dicarboxylic acid or derivative thereof is adipic acid.

32. A homogenous process according to claim 1 wherein the catalyst is regenerated in the presence of the water and hydrogen.

* * * * *